US011103680B2

(12) United States Patent
Cole

(10) Patent No.: US 11,103,680 B2
(45) Date of Patent: Aug. 31, 2021

(54) CATHETER INSERTION MECHANISM FOR A PATCH PUMP

(71) Applicant: Becton, Dickinson and Company, Franklin Lakes, NJ (US)

(72) Inventor: Russell Cole, River Vale, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 217 days.

(21) Appl. No.: 15/301,062

(22) PCT Filed: Apr. 23, 2015

(86) PCT No.: PCT/US2015/027361
§ 371 (c)(1),
(2) Date: Sep. 30, 2016

(87) PCT Pub. No.: WO2015/164648
PCT Pub. Date: Oct. 29, 2015

(65) Prior Publication Data
US 2017/0021137 A1    Jan. 26, 2017

Related U.S. Application Data

(60) Provisional application No. 61/983,969, filed on Apr. 24, 2014.

(51) Int. Cl.
*A61M 25/06* (2006.01)
*A61M 5/142* (2006.01)
(Continued)

(52) U.S. Cl.
CPC .... *A61M 25/0606* (2013.01); *A61M 5/14248* (2013.01); *A61M 25/0631* (2013.01);
(Continued)

(58) Field of Classification Search
CPC .... A61M 5/14248; A61M 2005/14252; A61M 2205/10; A61M 25/0606;
(Continued)

(56) References Cited

U.S. PATENT DOCUMENTS

| 4,894,054 A | * | 1/1990 | Miskinyar | A61M 5/14248 604/136 |
| 6,186,982 B1 | * | 2/2001 | Gross | A61M 5/14248 604/132 |

(Continued)

FOREIGN PATENT DOCUMENTS

| ES | 2365585 T3 | 10/2011 |
| JP | 2004-501721 A | 1/2004 |

(Continued)

*Primary Examiner* — William R Carpenter
*Assistant Examiner* — William R Frehe
(74) *Attorney, Agent, or Firm* — Dickinson Wright, PLLC

(57) ABSTRACT

Manual insertion device has retraction spring (202) and hollow septum configuration (224) implemented using barrel-shaped guides (108, 110) and a guiding boss (210) in insertion device housing (106), and provides a fluid path through alignment of septum openings, side-port openings and catheter openings upon complete catheter insertion. Button (200) causes manual insertion of introducer needle (204) and catheter (220) of a first barrel (108) into a skin surface, and loading of retraction spring (202) disposed in an adjacent second barrel (110). Once introducer needle (204) and catheter (220) are fully inserted, the introducer needle hub (206) is released and automatically retracted by release of the retraction spring (202), leaving the catheter (220) in the user's body. Septums (218, 224) and side-port openings (216, 228) in the button (200) and introducer needle (204) are thus aligned, creating an uninterrupted fluid path between a reservoir or pump and catheter (220).

7 Claims, 16 Drawing Sheets

(51) Int. Cl.
  *A61M 5/158* (2006.01)
  *A61M 39/02* (2006.01)

(52) U.S. Cl.
  CPC .......... *A61M 39/0247* (2013.01); *A61M 2005/14252* (2013.01); *A61M 2005/1585* (2013.01); *A61M 2205/10* (2013.01)

(58) Field of Classification Search
  CPC ...... A61M 2005/1585; A61M 39/0247; A61M 2005/14256; A61M 2005/1426; A61M 25/0612; A61M 25/0631; A61M 5/322; A61M 5/3232; A61M 2005/3239; A61M 2005/3235; A61M 2005/3236
  See application file for complete search history.

(56) References Cited

U.S. PATENT DOCUMENTS

| | | | | |
|---|---|---|---|---|
| 7,648,482 | B2* | 1/2010 | Edwards | A61M 5/2033 |
| | | | | 604/136 |
| 7,947,017 | B2* | 5/2011 | Edwards | A61M 5/19 |
| | | | | 604/144 |
| 9,731,069 | B2* | 8/2017 | Bene | A61M 5/158 |
| 9,878,110 | B2* | 1/2018 | Cole | A61M 5/5086 |
| 2002/0055711 | A1* | 5/2002 | Lavi | A61M 5/326 |
| | | | | 604/110 |
| 2005/0101912 | A1 | 5/2005 | Faust et al. | |
| 2009/0099521 | A1 | 4/2009 | Gravesen et al. | |
| 2010/0286609 | A1 | 11/2010 | Mahurkar | |
| 2011/0224621 | A1 | 9/2011 | Johansen et al. | |
| 2011/0300001 | A1* | 12/2011 | Murphy | A61M 5/14224 |
| | | | | 417/1 |
| 2011/0306929 | A1* | 12/2011 | Levesque | A61M 5/1684 |
| | | | | 604/150 |
| 2012/0022464 | A1* | 1/2012 | Zivkovic | A61M 5/31511 |
| | | | | 604/198 |
| 2013/0060233 | A1* | 3/2013 | O'Connor | A61M 5/158 |
| | | | | 604/506 |
| 2013/0102965 | A1* | 4/2013 | Teutsch | A61M 5/158 |
| | | | | 604/164.04 |
| 2013/0204191 | A1 | 8/2013 | Cindrich et al. | |
| 2014/0088509 | A1* | 3/2014 | Sonderegger | A61M 5/158 |
| | | | | 604/157 |

FOREIGN PATENT DOCUMENTS

| | | |
|---|---|---|
| JP | 2014-507227 A | 3/2014 |
| WO | WO-0202165 A2 | 1/2002 |
| WO | WO-2010066588 A1 | 6/2010 |
| WO | WO-2012108959 A1 | 8/2012 |
| WO | WO-2014011879 A2 | 1/2014 |

* cited by examiner

CATHETER INSERTION MECHANISM FOR A PATCH PUMP

CROSS-REFERENCE TO RELATED APPLICATION

This application claims the benefit under 35 U.S.C. § 119(e) of U.S. Provisional Application No. 61/983,969, filed on Apr. 24, 2014 in the U.S. Patent and Trademark Office, the disclosure of said application being incorporated herein by reference in its entirety.

FIELD OF THE INVENTION

The present invention relates generally to medical infusion systems, such as an insulin infusion device or insertion device, where a simple, low-profile and low-part count manual insertion device is provided with a retraction spring and hollow septum configuration implemented using multiple barrel-shaped guides and at least one guiding boss in the insertion device housing which allows for a much smaller retraction spring to be used than in a single-barrel configuration, and provides a fluid path through alignment of septum openings, side-port openings and catheter openings at the point of complete catheter insertion which eliminates the need for a tubing connection to the catheter, movable during insertion, and the large space necessary in which such tubing would travel.

BACKGROUND OF THE INVENTION

Diabetes is a group of diseases characterized by high levels of blood glucose resulting from the inability of diabetic patients to maintain proper levels of insulin production when required. Persons with diabetes will require some form of daily insulin therapy to maintain control of their glucose levels. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient.

For the treatment of type 1 diabetes, there are two principal methods of daily insulin therapy. In the first method, diabetic patients use syringes or insulin pens to self-inject insulin when needed. This method requires a needle stick for each injection, and the diabetic patient may require three to four injections daily. The syringes and insulin pens that are used to inject insulin are relatively simple to use and cost effective.

Another effective method for insulin therapy and managing diabetes is infusion therapy or infusion pump therapy in which an insulin pump is used. The insulin pump can provide continuous infusion of insulin to a diabetic patient at varying rates in order to more closely match the functions and behavior of a properly operating pancreas of a non-diabetic person that produces the required insulin, and the insulin pump can help the diabetic patient maintain his/her blood glucose level within target ranges based on the diabetic patient's individual needs.

Infusion pump therapy requires an infusion cannula, typically in the form of an infusion needle or a flexible catheter, that pierces the diabetic patient's skin and through which infusion of insulin takes place. Infusion pump therapy offers the advantages of continuous infusion of insulin, precision dosing, and programmable delivery schedules.

In infusion therapy, insulin doses are typically administered at a basal rate and in a bolus dose. When insulin is administered at a basal rate, insulin is delivered continuously over 24 hours in order to maintain the diabetic patient's blood glucose levels in a consistent range between meals and rest, typically at nighttime. Insulin pumps may also be capable of programming the basal rate of insulin to vary according to the different times of the day and night. In contrast, a bolus dose is typically administered when a diabetic patient consumes a meal, and generally provides a single additional insulin injection to balance the consumed carbohydrates. Insulin pumps may be configured to enable the diabetic patient to program the volume of the bolus dose in accordance with the size or type of the meal that is consumed by the diabetic patient. In addition, insulin pumps may also be configured to enable the diabetic patient to infuse a correctional or supplemental bolus dose of insulin to compensate for a low blood glucose level at the time when the diabetic patient is calculating the bolus dose for a particular meal that is to be consumed.

Insulin pumps advantageously deliver insulin over time rather than in single injections, typically resulting in less variation within the blood glucose range that is recommended. In addition, insulin pumps may reduce the number of needle sticks which the diabetic patient must endure, and improve diabetes management to enhance the diabetic patient's quality of life.

Typically, regardless of whether a diabetic patient uses multiple direct injections (MDIs) or a pump, the diabetic patient takes fasting blood glucose medication (FBGM) upon awakening from sleep, and also tests for glucose in the blood during or after each meal to determine whether a correction dose is required. In addition, the diabetic patient may test for glucose in the blood prior to sleeping to determine whether a correction dose is required, for instance, after eating a snack before sleeping.

To facilitate infusion therapy, there are generally two types of insulin pumps, namely, conventional pumps and patch pumps. Conventional pumps require the use of a disposable component, typically referred to as an infusion set, tubing set or pump set, which conveys the insulin from a reservoir within the pump into the skin of the user. The infusion set consists of a pump connector, a length of tubing, and a hub or base from which a cannula, in the form of a hollow metal infusion needle or flexible plastic catheter extends. The base typically has an adhesive that retains the base on the skin surface during use. The cannula can be inserted onto the skin manually or with the aid of a manual or automatic insertion device. The insertion device may be a separate unit required by the user.

Another type of insulin pump is a patch pump. Unlike a conventional infusion pump and infusion set combination, a patch pump is an integrated device that combines most or all of the fluidic components, including the fluid reservoir, pumping mechanism and mechanism for automatically inserting the cannula, in a single housing which is adhesively attached to an infusion site on the patient's skin, and does not require the use of a separate infusion or tubing set. A patch pump containing insulin adheres to the skin and delivers the insulin over a period of time via an integrated subcutaneous cannula. Some patch pumps may wirelessly communicate with a separate controller device (as in one device sold by Insulet Corporation under the brand name OmniPod®), while others are completely self-contained. Such devices are replaced on a frequent basis, such as every three days, when the insulin reservoir is exhausted or complications may otherwise occur, such as restriction in the cannula or the infusion site.

As patch pumps are designed to be a self-contained unit that is worn by the diabetic patient, it is preferable to be as small as possible so that it does not interfere with the activities of the user. Thus, in order to minimize discomfort to the user, it would be preferable to minimize the overall thickness of the patch pump. However, in order to minimize the thickness of the patch pump, its constituent parts should be reduced as much as possible. One such part is the insertion mechanism for automatically inserting the cannula into the user's skin.

In order to minimize the height of the insertion mechanism, some conventional insertion mechanisms are configured to insert the cannula at an acute angle from the surface of the skin, e.g. 30-45 degrees. However, it may be preferable to insert the cannula perpendicular or close to the perpendicular from the surface of the skin, since this would require the minimum length of cannula insertion. In other words, with the minimum length of cannula being inserted into the user's skin, the user can experience greater comfort and fewer complications, such as premature kinking of the cannula. But one problem with configuring the insertion mechanism to insert the cannula perpendicular to the surface of the skin is that this may increase the overall height of the insertion mechanism, and therefore of the patch pump itself.

Accordingly, a need exists for an improved insertion mechanism for use in a limited space environment, such as in the patch pump, that can cost-effectively insert a cannula vertically or close to perpendicularly into the surface of a user's skin, while minimizing or reducing its height, in order to reduce the overall height of the device the insertion mechanism is incorporated into, such as a patch pump.

SUMMARY OF THE INVENTION

An object of the present invention is to substantially address the above and other concerns, and provide advanced, improved, and novel components and elements of an insertion device that facilitates insertion of the in-dwelling or soft catheter and retract the introducer needle, while reducing the number of components required for the construction and use of the insertion device.

Another object of the present invention is to provide a manual insertion device with at least automatic introducer needle retraction, such that the part count of the exemplary embodiments is lowered and which serves to keep part production costs low and simplify device assembly.

Another object of the present invention is to provide a manual insertion device with at least automatic introducer needle retraction using a retraction spring configuration that is implemented using multiple barrel-shaped guides and at least one guiding boss in the insertion device housing which allows for a much smaller retraction spring to be used, such that the device is smaller and more compact.

Another object of the present invention is to provide a manual insertion device with at least automatic introducer needle retraction using an alignment of septum openings, side-port openings and catheter openings, preferably at the point of complete catheter insertion to provide a fluid path which eliminates the need for a tubing connection to the catheter, movable during insertion, and the large space necessary in which such tubing would travel.

Another object of the present invention is to provide a manual insertion device with at least automatic introducer needle retraction and insertion button locking to provide needle shielding and maintain insertion of the catheter.

These and other objects are substantially achieved by providing an insertion device with a retraction spring and hollow septum configuration implemented using multiple barrel-shaped guides and at least one guiding boss in the insertion device housing, and that provides a fluid path through alignment of septum openings, side-port openings and catheter openings only at the point of complete catheter insertion. A button of the insertion device is used to manually insert the introducer needle and catheter of a first barrel into a skin surface, and simultaneously load the retraction spring disposed in an adjacent second barrel. Once the introducer needle and catheter have been fully inserted, the introducer needle hub is released and is automatically retracted by the retraction spring, leaving the catheter in the body of the user. At this point, a number of septums and side-port openings provided in the button and introducer needle are aligned, thereby creating an uninterrupted fluid path between a reservoir or pump, and catheter.

BRIEF DESCRIPTION OF THE DRAWINGS

The various objects, advantages and novel features of the exemplary embodiments of the present invention will be more readily appreciated from the following detailed description when read in conjunction with the appended drawings, in which.

Throughout the drawings, like reference numerals will be understood to refer to like parts, components and structures.

DETAILED DESCRIPTION OF THE EXEMPLARY EMBODIMENTS

The exemplary embodiments of the present invention described below provide novel means of providing one or more insertion device elements that are configured to insert a catheter up to 6 mm into a skin surface, but embodiments are not limited thereto. The insertion device provides an insertion button for manual insertion of the catheter and introducer needle, a retraction spring for automatic retraction of the introducer needle, and hollow septums, side-ported introducer needles and side-ported insertion button bodies for tubeless fluid path establishment, implemented using multiple barrel-shaped guides and at least one guiding boss in the insertion device housing, and using septum openings, side-port insertion button and introducer needle openings that are aligned only at the point of complete catheter insertion for establishing a tubeless fluid path.

A button of the insertion device is used to manually insert the introducer needle and catheter through an insertion button barrel and into a skin surface, and load, preferably simultaneously, a retraction spring disposed in an adjacent retraction spring barrel. Once the introducer needle and catheter have been fully inserted, the introducer needle hub is released and is automatically retracted by the retraction spring, leaving the catheter in the body of the user. A side-ported distal end of the introducer needle is left in the catheter and aligns with one or more of the septums and side-port openings provided in the insertion button at the point of complete catheter insertion and introducer needle retraction, thereby creating an uninterrupted fluid path between a reservoir or pump, and the catheter in the body of the user.

Figure 1:
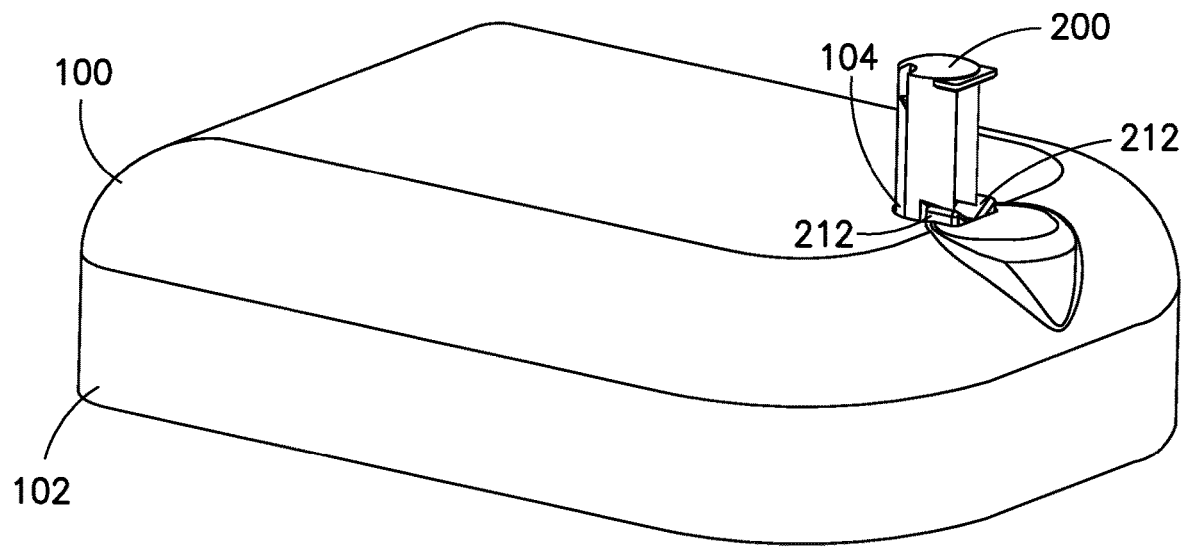
FIG. 1 is a view of an exemplary insertion device in a pre-activation state in accordance with an embodiment of the present invention.
Figure 2:
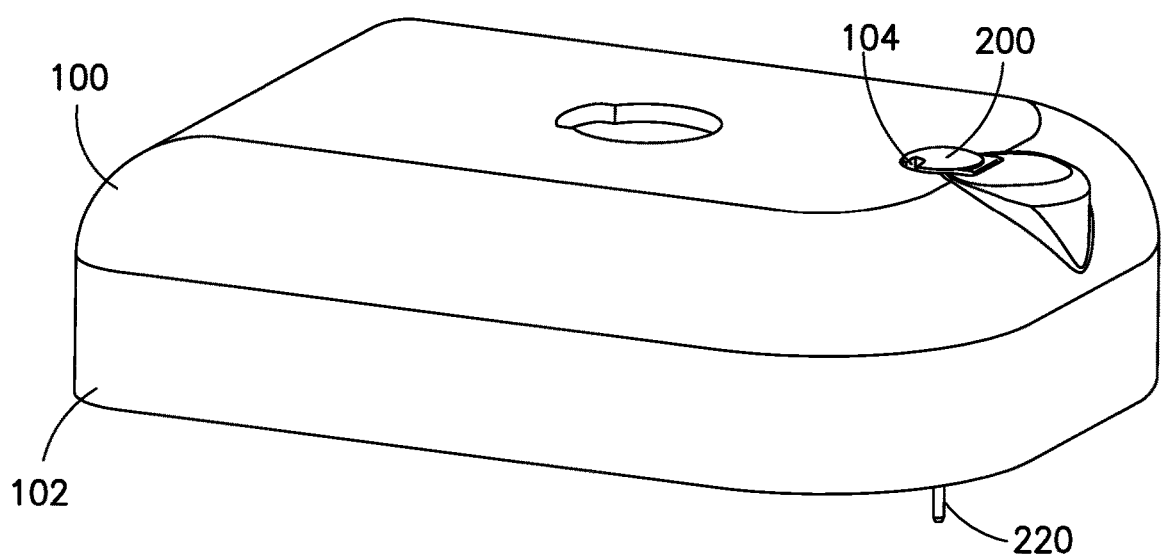
FIG. 2 is a view of the insertion device of FIG. 1 in a post-activation state in accordance with an embodiment of the present invention.
Figure 3:
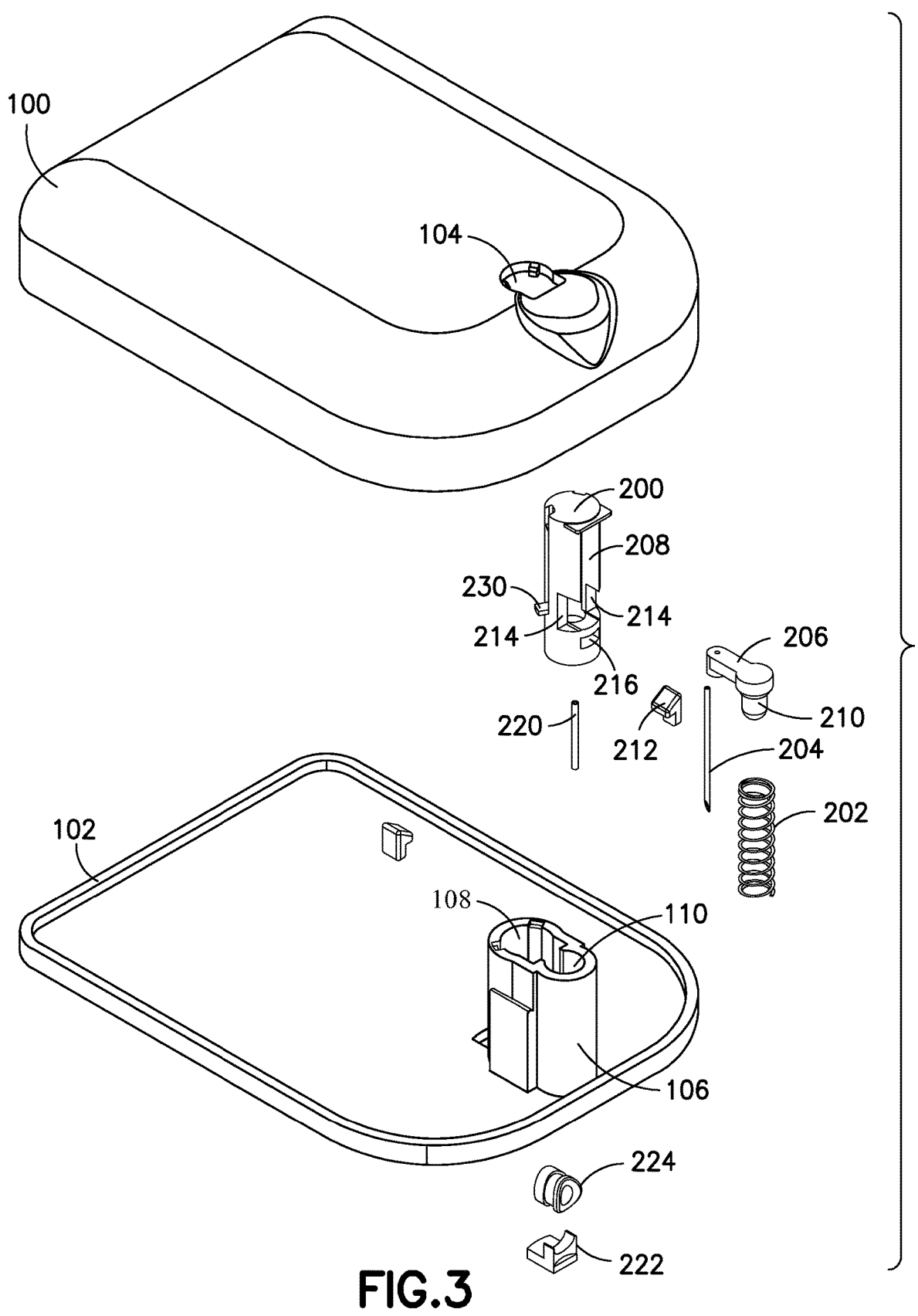
FIG. 3 is an exploded view of the insertion device of FIG. 1 in accordance with an embodiment of the present invention.

FIG. 1 is a view of an exemplary insertion device in a pre-activation state and FIG. 2 is a view of the insertion device of FIG. 1 in a post-activation state in accordance with an embodiment of the present invention. FIG. 3 is an exploded view of the insertion device of FIG. 1.

The insertion device includes a top housing 100 and base 102. The top housing 100 is shown having an opening 104 through a top surface and from which a user-accessible, and user-acutatable manual insertion button 200 slidably extends. In the following embodiments, the top housing 100, button 200, and base 102, can be manufactured from plastic materials, such as ABS or PETG, but embodiments are not limited thereto.

Figure 4:
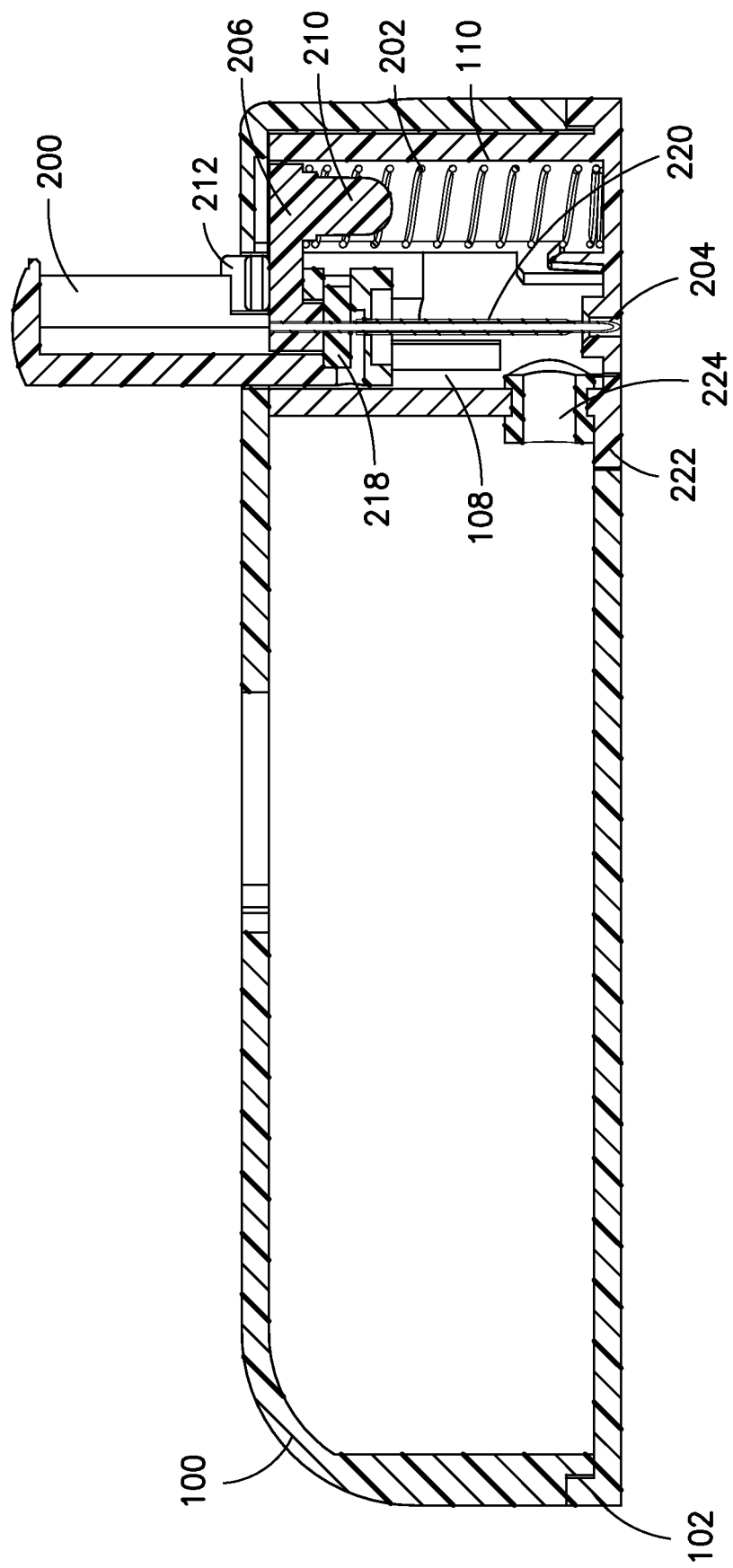
FIG. 4 is an enlarged sectional view of the insertion device of FIG. 1 in the pre-activation state in accordance with an embodiment of the present invention.

The insertion button 200 of the insertion device is slidably contained within a mechanism housing 106 provided on the base 102. The mechanism housing 106 is preferably comprised of two conjoined cylinders, guides or barrels, including an insertion button barrel, or first barrel 108, that slidably receives and guides the insertion button 200, and an adjacent retraction spring barrel, or second barrel 110, that constrains a retraction spring 202, as illustrated in FIG. 4. The spring 202 can be manufactured using metal, such as stainless steel, such as CSC stainless 70065, but embodiments are not limited thereto, and could be manufactured using plastic or any suitable material.

The first barrel 108 and adjacent second barrel 110 extend between the base 202 and top housing 100 and are conjoined to provide access between each. As described in greater detail below, the insertion button 200 is slidably captured within the first barrel 108 and the spring 202 is compressably captured within the adjacent second barrel 110, and the introducer needle hub 206 is extended to access both the first barrel 108 for insertion button engagement, and the second barrel 110 for retraction spring engagement.

The insertion button 200 of the insertion device is used to manually insert the introducer needle 204 and catheter 220 through the first barrel 108 and into a skin surface, and simultaneously load the retraction spring 202 disposed in the adjacent second barrel 110. To do so, the insertion device includes an introducer needle subassembly that is releasably secured to the insertion button 200. The introducer needle subassembly is formed using a cannula or introducer needle 204 that is press-fit, glued or otherwise secured to the introducer needle hub 206. The introducer needle 204 can be a hollow, 27 G needle or cannula manufactured using 304 stainless steel, and the introducer needle hub 206 can be manufactured using PETG, but embodiments are not limited thereto.

The introducer needle hub 206 comprises the needle end having secured thereto the introducer needle 204 and which is slidably disposed in a groove or slot 208 in the insertion button 200 and, wherein the introducer needle hub 206 and insertion button 200 are together slidably disposed in the first barrel 108. At an opposite end, the introducer needle hub 206 comprises the spring end, having a rounded profile configured to slidably fit the second barrel inner diameter and having a boss 210 extending therefrom and into the second barrel 110. The boss 210 is configured to constrain the retraction spring 202 in the second barrel 110, and translates through the middle of the spring 202 during compression to prevent the spring 202 from buckling.

Figure 7:
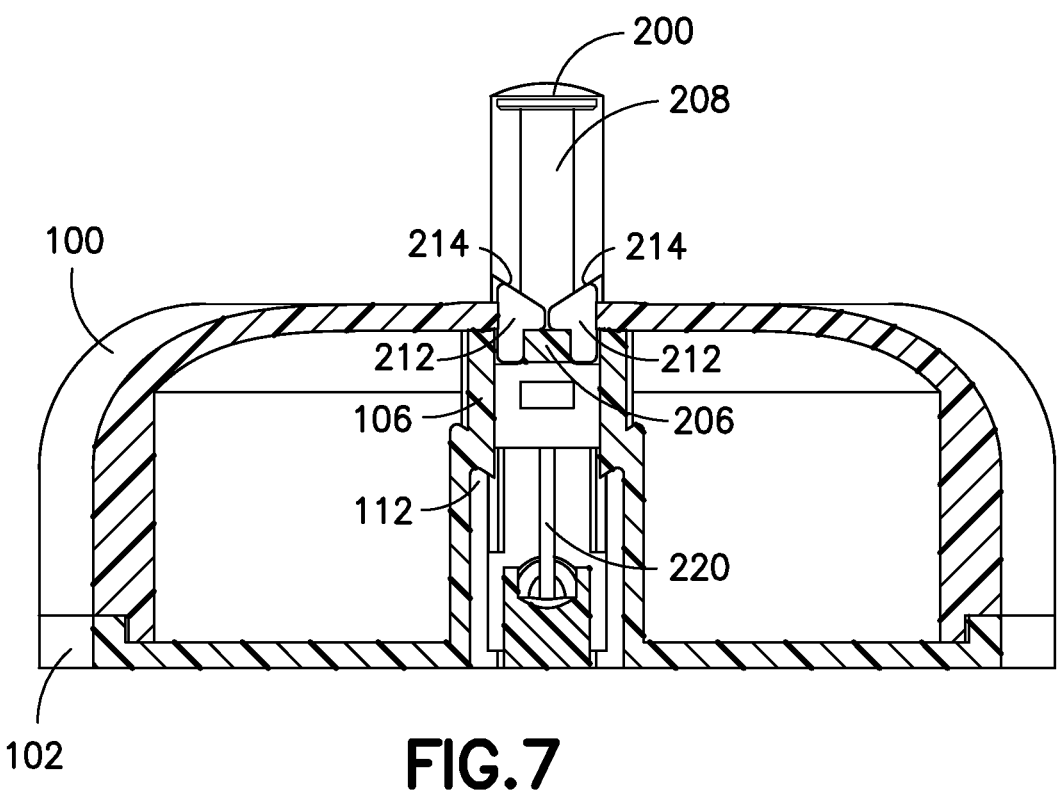
FIG. 7 is another enlarged sectional view of the insertion device of FIG. 1 illustrating a plurality of interference pieces disposed between the introducer needle subassembly, insertion button and walls of the insertion button barrel, thereby securing the introducer needle subassembly to the insertion button in the pre-activation state in accordance with an embodiment of the present invention.
Figure 8:
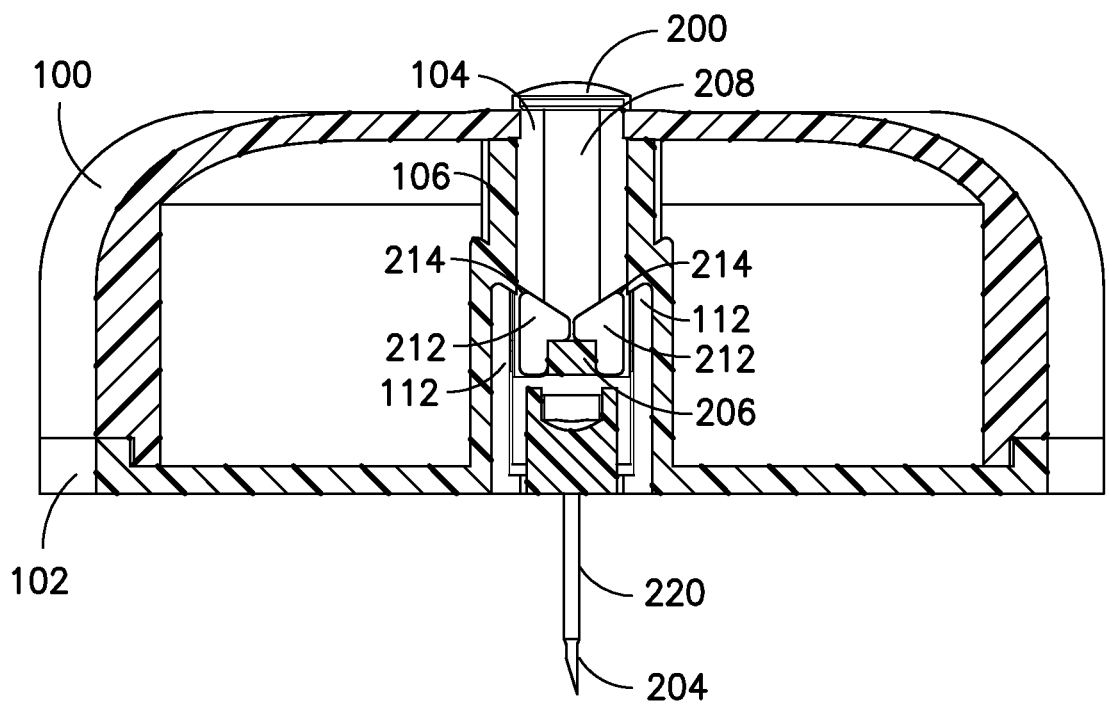
FIG. 8 is another enlarged sectional view of the insertion device of FIG. 1 illustrating the plurality of interference pieces reaching an expanded portion of the insertion button barrel during activation in accordance with an embodiment of the present invention.
Figure 10:
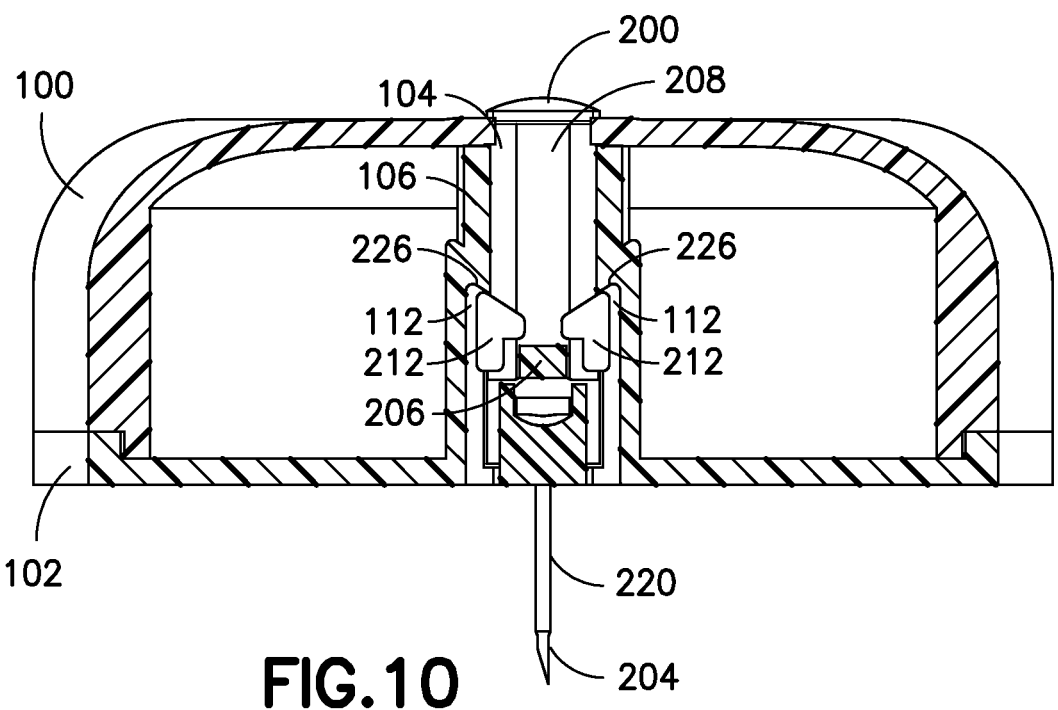
FIG. 10 is another enlarged sectional view of the insertion device of FIG. 1 illustrating the plurality of interference pieces beginning slidable displacement into the expanded portion of the insertion button barrel during activation in accordance with an embodiment of the present invention.
Figure 12:
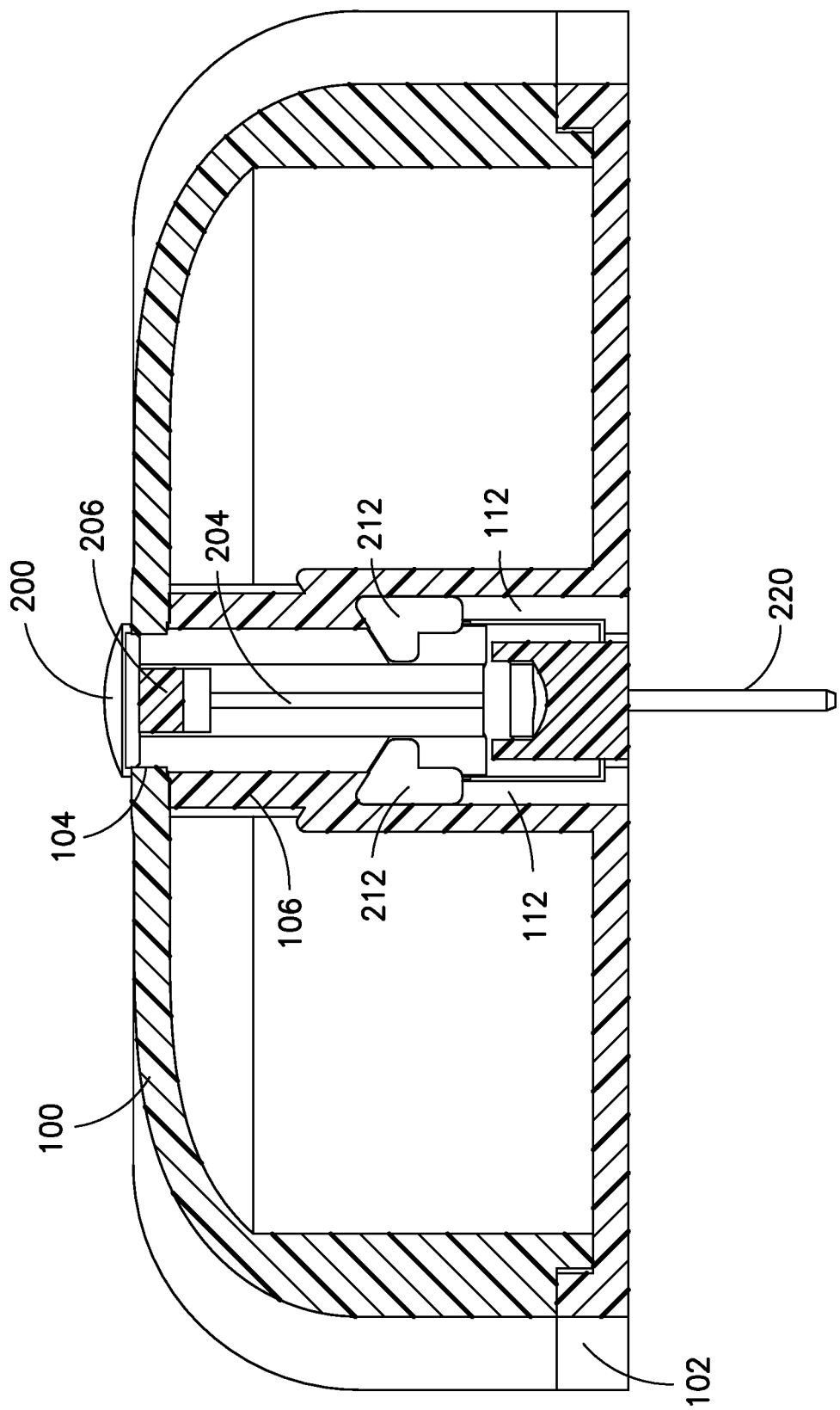
FIG. 12 is another enlarged sectional view of the insertion device of FIG. 1 illustrating the plurality of interference pieces slidably displaced into the expanded portion of the insertion button barrel in the post-activation state, thereby releasing the introducer needle subassembly from the insertion button and retracted within a center opening of the insertion button by the retraction spring of the retraction spring barrel in accordance with an embodiment of the present invention.

To permit the insertion button 200 of the insertion device to manually insert the introducer needle and catheter through the first barrel 108 and into a skin surface, and simultaneously load the retraction spring 202 disposed in the adjacent second barrel 110, the introducer needle hub 206 is releasably held by and prevented from slidably moving relative to the insertion button 200. As shown in FIGS. 7, 8, 10 and 12, interference pieces 212 are placed on a top surface of the introducer needle hub 206, and the introducer needle hub 206 and pieces 212 are placed in slots 214 of the insertion button 200. The insertion button 200 and introducer needle hub 206 are then placed in the first barrel 108 of the mechanism housing 106. At the same time, the opposite end of the introducer needle hub 206 is placed in the second barrel 110 of the mechanism housing 106 over the retraction spring 202. FIG. 7 is an enlarged sectional view illustrating the interference pieces 212 disposed between the introducer needle hub 206, insertion button 200 and walls of the first barrel 108, thereby securing the introducer needle subassembly to the insertion button in the pre-activation state. FIG. 8 illustrates the interference pieces 212 reaching an expanded portion 112 of the first barrel 108 during activation and FIG. 10 illustrates interference pieces 212 beginning slidable displacement into the expanded portion 112 of the first barrel 108 during activation. FIG. 12 illustrates the interference pieces 212 slidably displaced into the expanded portion 112 of the first barrel 108 in the post-activation state, thereby releasing the introducer needle hub 206 from the insertion button 200 and retracted within the center opening 208 of the insertion button 200 by the retraction spring 202 of the second barrel 110.

Figure 9:
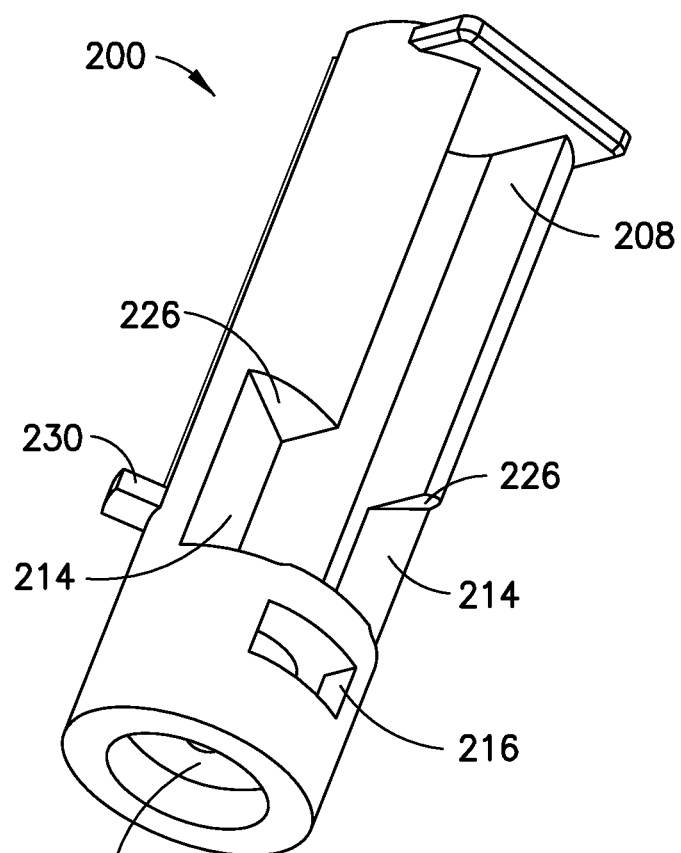
FIG. 9 is an enlarged view of the insertion button of the insertion device of FIG. 1 illustrating inclined slots in which the plurality of interference pieces are slidably disposed, the insertion button holding detent, side-port and button septum therein, in accordance with an embodiment of the present invention.

As shown in greater detail in FIGS. 7 and 9, the slots 214 of the button 200 have an inclined upper surface 226 that mates with an inclined upper surface of the interference pieces 212 and, when in the complete insertion position, align with inclined upper surfaces of the expanded portion 112 of the first barrel 108. FIG. 9 is an enlarged view of the insertion button of the insertion device of FIG. 1 illustrating inclined slots in which the plurality of interference pieces are slidably disposed, the insertion button holding detent, side-port and button septum therein, in accordance with an embodiment of the present invention.

When the insertion button 200 is slidably disposed in the first barrel 108, the interference pieces 212 in slots 214 are prevented from sliding along the incline 226 toward an outward position even when urged to do so by the retraction spring 202 being compressed. The interference pieces 212 are biased to translate outwards but are constrained by the walls of the first barrel 108 during insertion. As the insertion button 200, interference pieces 212 and introducer needle hub 206 travel downward in the first barrel 108, at complete insertion, the interference pieces 212 reach and slide into the widened portion 112 of the first barrel 108, thereby decoupling. Once decoupled, the spring retracts the introducer needle.

In an exemplary embodiment, the insertion button 200 includes the inner diameter or channel 208 in which the introducer needle hub 206 is slidably disposed. The introducer needle hub 206 is initially prevented from sliding within the inner channel 208 of the insertion button 200 by the interference pieces 212, which are constrained during downward movement of the insertion button 200 by the walls of the first barrel 108, such that the insertion button 200 can be used to simultaneously move the catheter 220 and introducer needle 204 and hub 206 downward for the insertion of the introducer needle 204 and catheter 220.

Figure 11:
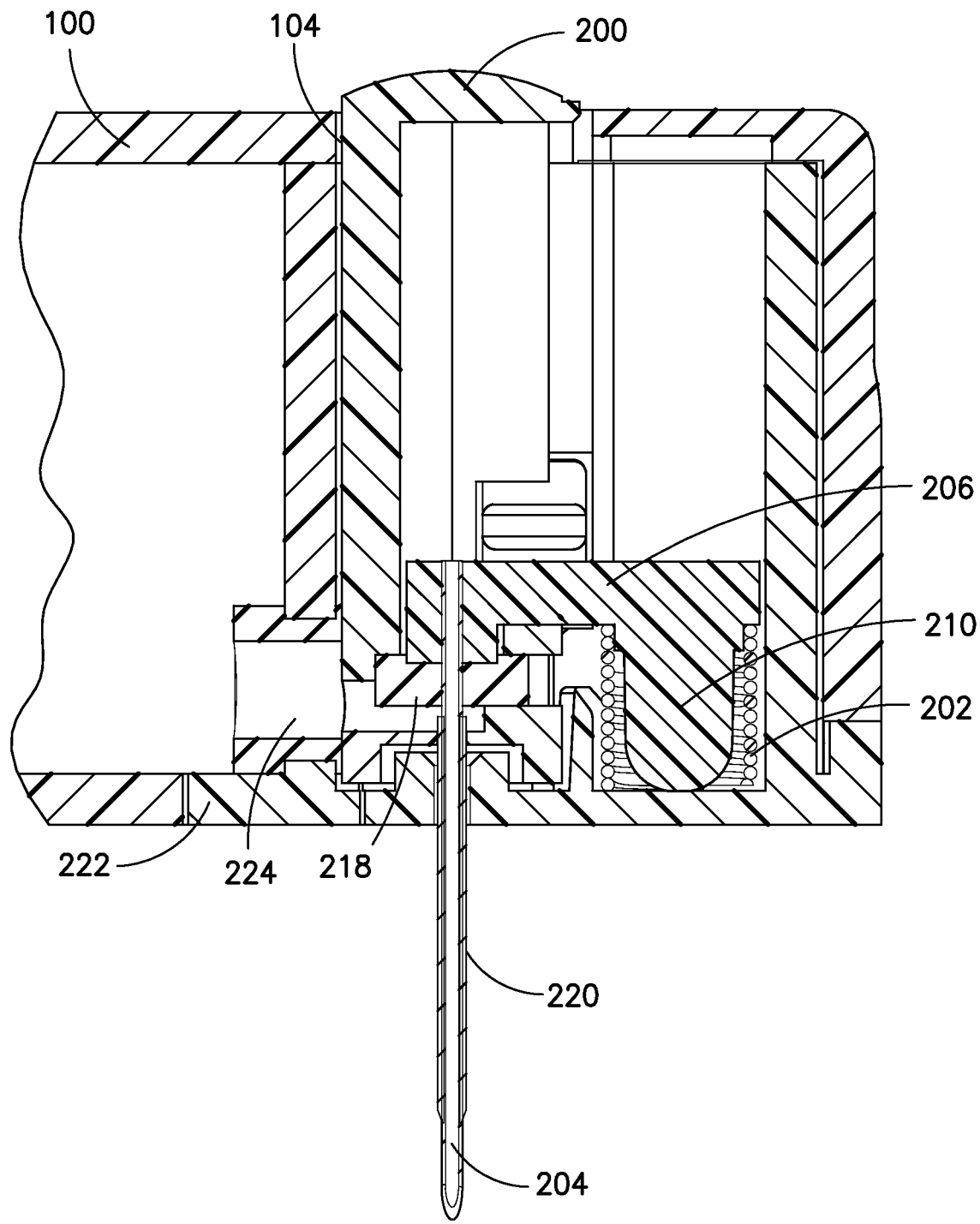
FIG. 11 is another enlarged sectional view of the insertion device of FIG. 1 illustrating the compression of the retraction spring in the retraction spring barrel by the introducer needle subassembly in accordance with an embodiment of the present invention.
Figure 15:
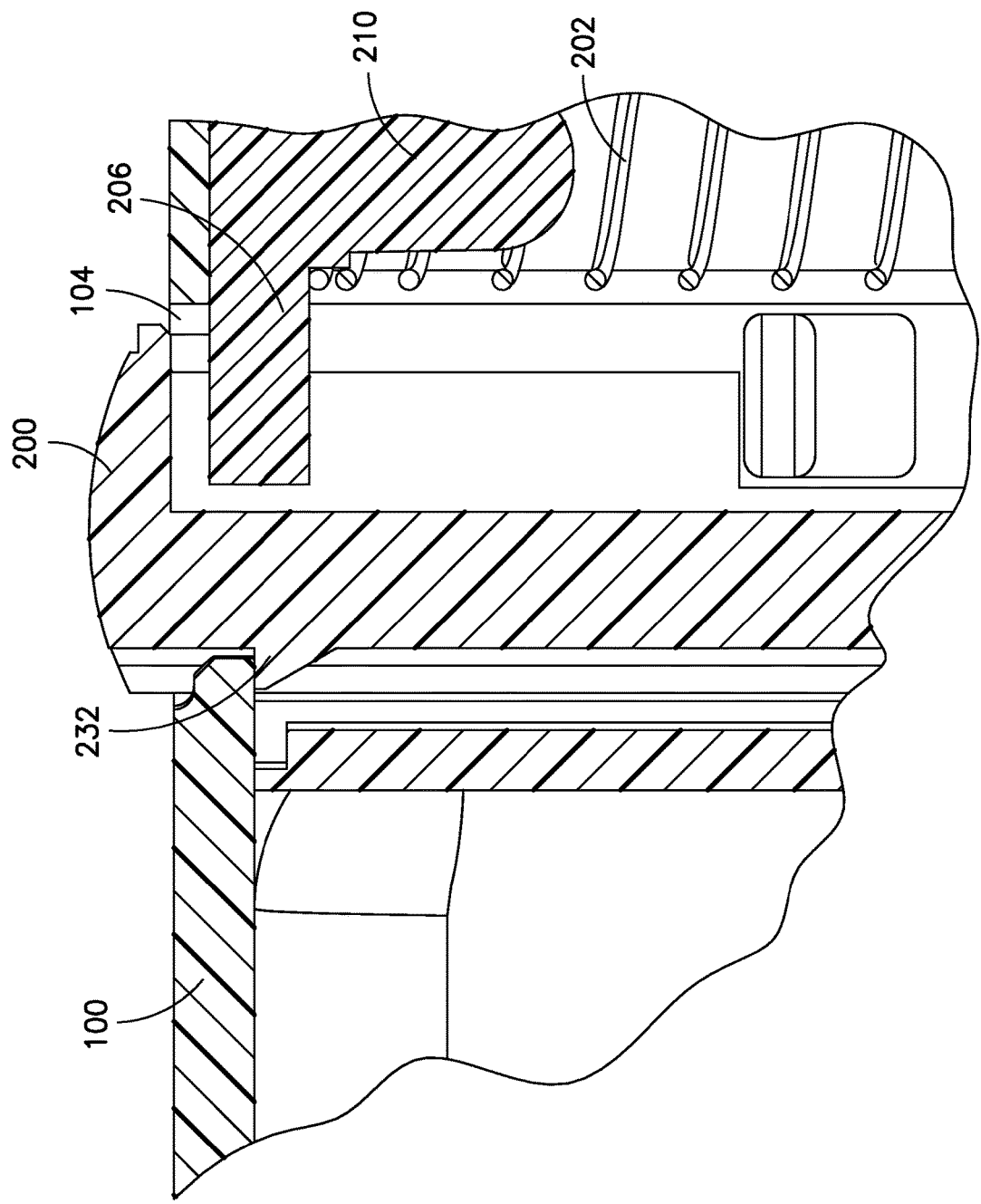
FIG. 15 is another enlarged sectional view of the insertion device of FIG. 1 illustrating an insertion button holding detent in the post-activation state in accordance with an embodiment of the present invention.

The interference pieces 212 travel within the inner diameter of the first barrel 108 and are engaged with the insertion button 200 using the inclines such that the compression of the retraction spring 202 (illustrated in FIG. 11) also results in the interference pieces 212 being biased to translate outward against the walls of the first barrel 108. At a point corresponding with complete insertion of the catheter, the walls of the first barrel 108 expand, permitting the bias of the interference pieces 212 to slidably move the interference pieces 212 along the inclines of the insertion button 200 and inclines of the expanded channel 112, into the expanded channel 112, and releasing the introducer needle hub 206. Once released, the compressed retraction spring 202 retracts the introducer needle hub 206, leaving the inserter button 200 and catheter 220 in place. In the exemplary embodiments of the present invention, the inserter button 200 and catheter 220 in place can be locked in place as described in greater detail below in regard to FIG. 15.

During assembly, the spring 202 is captured between boss 210 of the introducer needle hub 206 and a bottom of the second barrel 110 of the mechanism housing 106. In doing so, the spring 202 exerts an expansion force between the introducer needle hub 206 and a bottom of the barrel 110 of the mechanism housing 106. The rounded, boss 210 is provided with a diameter and length to center and align the spring 202 during operation. The spring 202 can be partially preloaded during assembly of the insertion device to ensure complete retraction of the introducer needle. For example, the retraction spring 202 can be minimally loaded before use to ensure that the introducer needle 202 retracts into the device completely. The spring 202 loads further during insertion. Providing minimally loaded springs and not fully loaded springs in the insertion device, reduces the risk associated with sterilizing and storing loaded springs and simplifies the design.

In an exemplary embodiment described below, a side-ported distal end of the introducer needle 204 is left in the catheter 220 and aligns with one or more of the septums and side-port openings provided in the insertion button at the point of complete catheter insertion and introducer needle retraction, thereby creating an uninterrupted fluid path between a reservoir or pump, and the catheter in the body of the user As shown in FIGS. 3 and 9, the insertion button 200 further includes a side-port 216 having therein a side-port insertion button septum 218 and extending therefrom, a catheter 220, such as a 24 G plastic catheter manufactured using FEP, but embodiments are not limited thereto. To complete the fluid path upon compete insertion of the catheter 220 and retraction of the introducer needle 204 at the post-activation state, the base 102 further incudes a tubing connector member 222 and a hollow septum 224.

Figure 5:
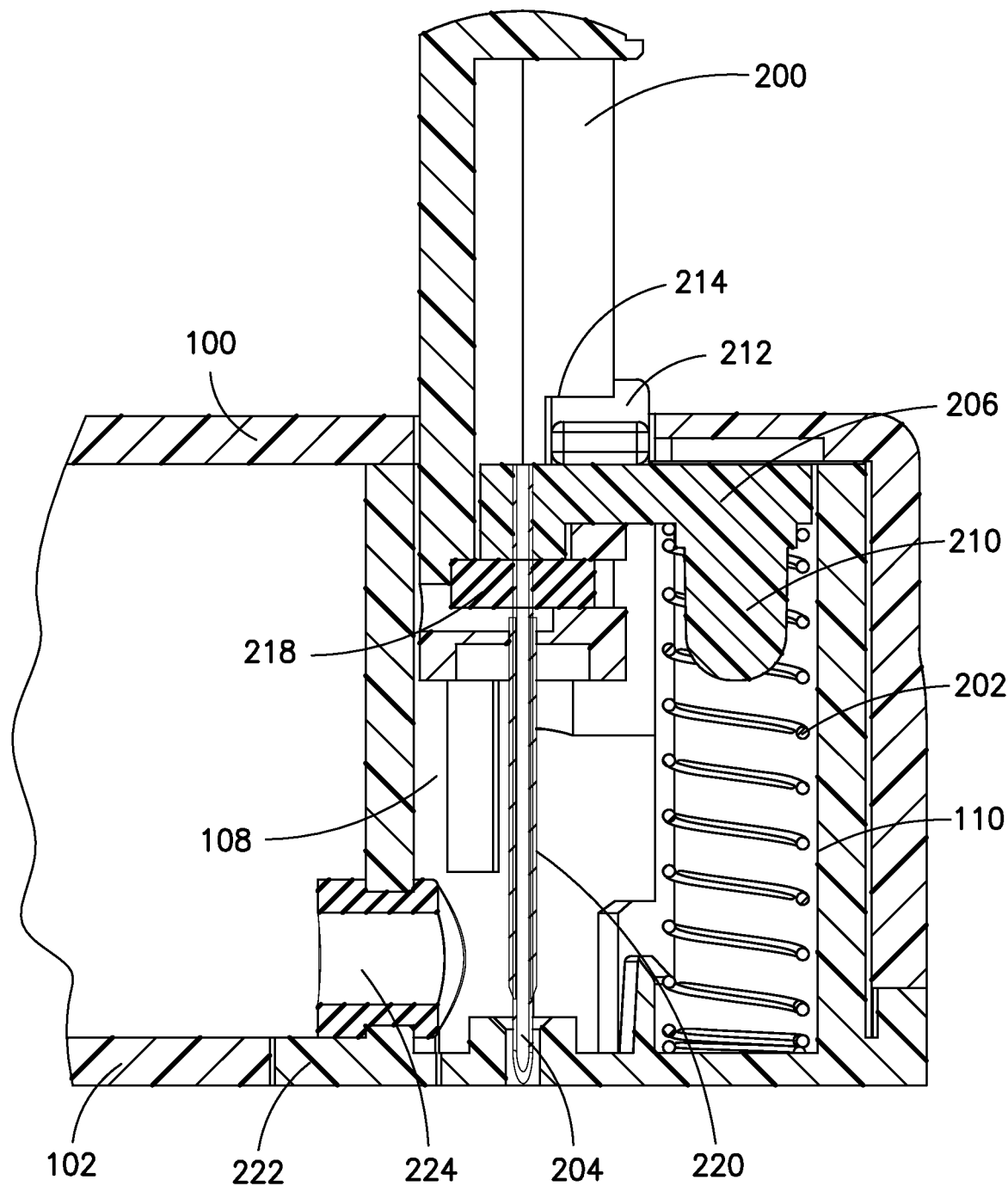
FIG. 5 is another enlarged sectional view of the insertion device of FIG. 1 in the pre-activation state in accordance with an embodiment of the present invention.
Figure 13:
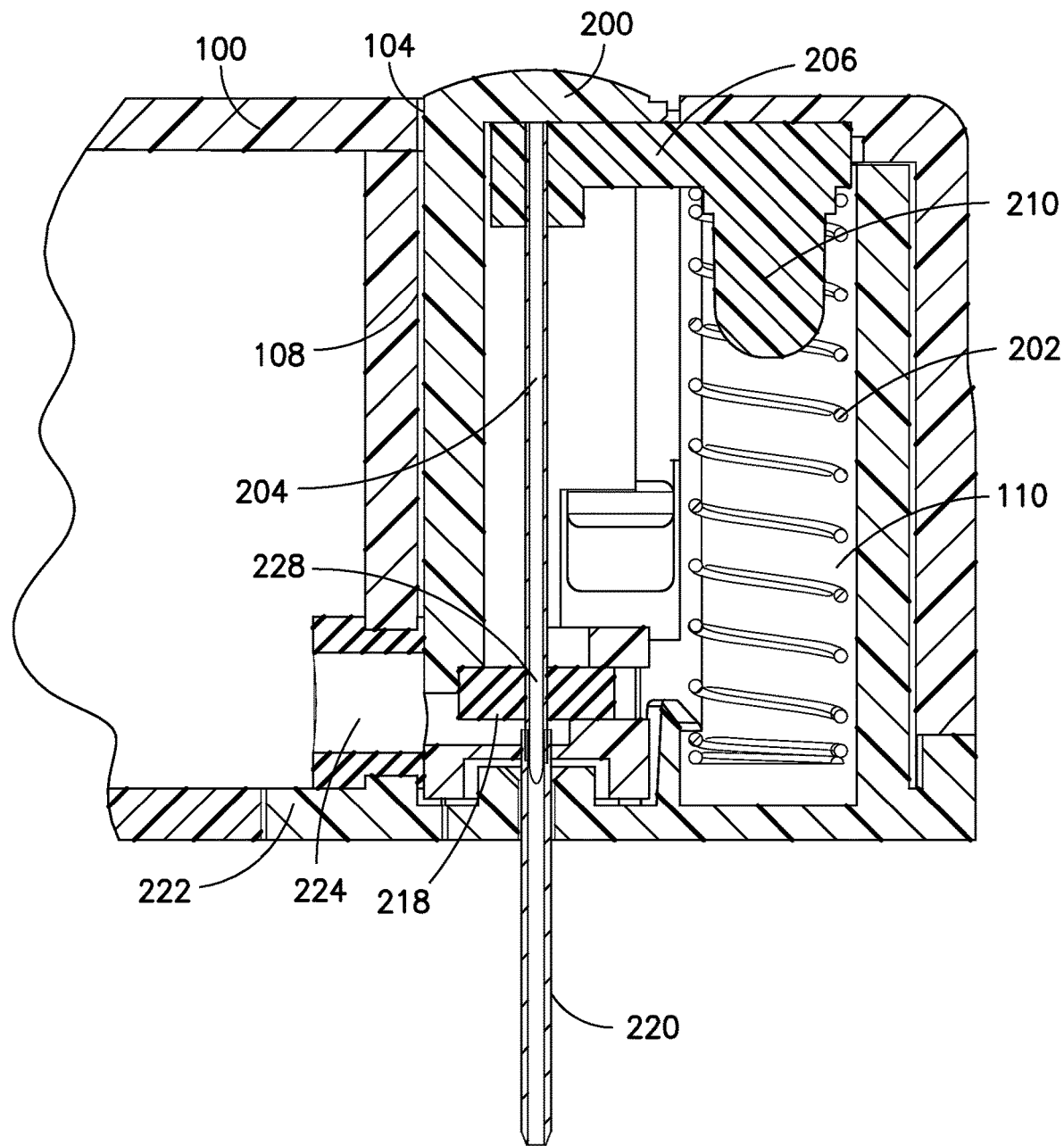
FIG. 13 is another enlarged sectional view of the insertion device of FIG. 1 illustrating the introducer needle subassembly retracted within the center opening of the insertion button and the alignment of septum openings, side-port openings and catheter openings at the point of complete catheter insertion in the post-activation state in accordance with an embodiment of the present invention.
Figure 14:
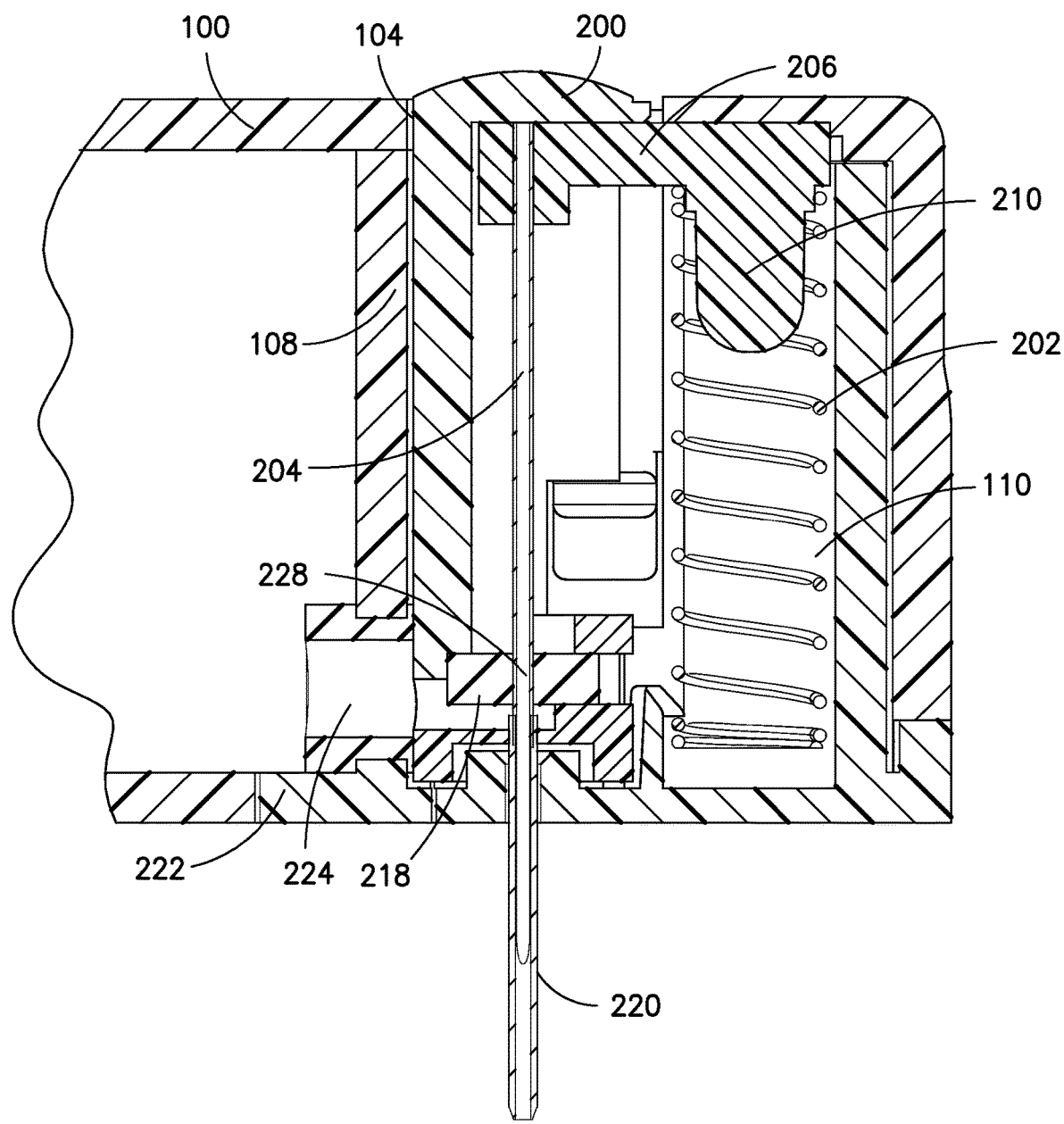
FIG. 14 is another enlarged sectional view of the insertion device of FIG. 1 illustrating the alignment of septum openings, side-port openings and catheter openings at the point of complete catheter insertion in the post-activation state in accordance with an embodiment of the present invention.

As shown in FIGS. 4 and 5, the catheter 220 is not connected to any fluid path before insertion. FIGS. 4 and 5 are enlarged sectional views of the insertion device of FIG. 1 in the pre-activation state in accordance with an embodiment of the present invention. When the catheter 220 and button 200 move into a complete insertion position, and the introducer needle hub 206 and introducer needle 204 are retracted, a septum well created by the side-port 216 of the insertion button 200, side-port insertion button septum 218, side-port opening 228 in the introducer needle 204 and catheter 220 form a sealed, uninterrupted fluid path to a pump or reservoir (not shown) via the hollow septum 224 as shown in FIGS. 13 and 14. FIGS. 13 and 14 are enlarged sectional views of the insertion device of FIG. 1 illustrating the introducer needle subassembly retracted within the center opening of the insertion button and the alignment of septum openings, side-port openings and catheter openings at the point of complete catheter insertion in the post-activation state in accordance with an embodiment of the present invention.

Specifically, the insertion button 200 contains a radial hole or side-port 216 which aligns with the flexible hollow septum 224 of the base 102 in the post-activation state. Within the insertion button 200, the alignment includes the aligned openings of the side-port insertion button septum 218, side-port opening 228 in the introducer needle 204, and catheter 220. The aligned openings form a sealed, uninterrupted fluid path to a pump or reservoir. The hollow septum 224 is connected to a reservoir or pump via tubing or tube set (not shown). The introducer needle 204 includes the side-port opening 228, and a proximal end of the introducer needle 228 can be occluded (not shown) to create a closed fluid path. Accordingly, instead of a metal wedge which is commonly used to attach a plastic catheter to a medical device, embodiments of the present invention can use a nail head-like introducer needle or catheter feature. This allows for a smaller attachment feature which helps keep the overall height of the mechanism small. An introducer needle septum can be provided to seal the septum well.

Figure 6:
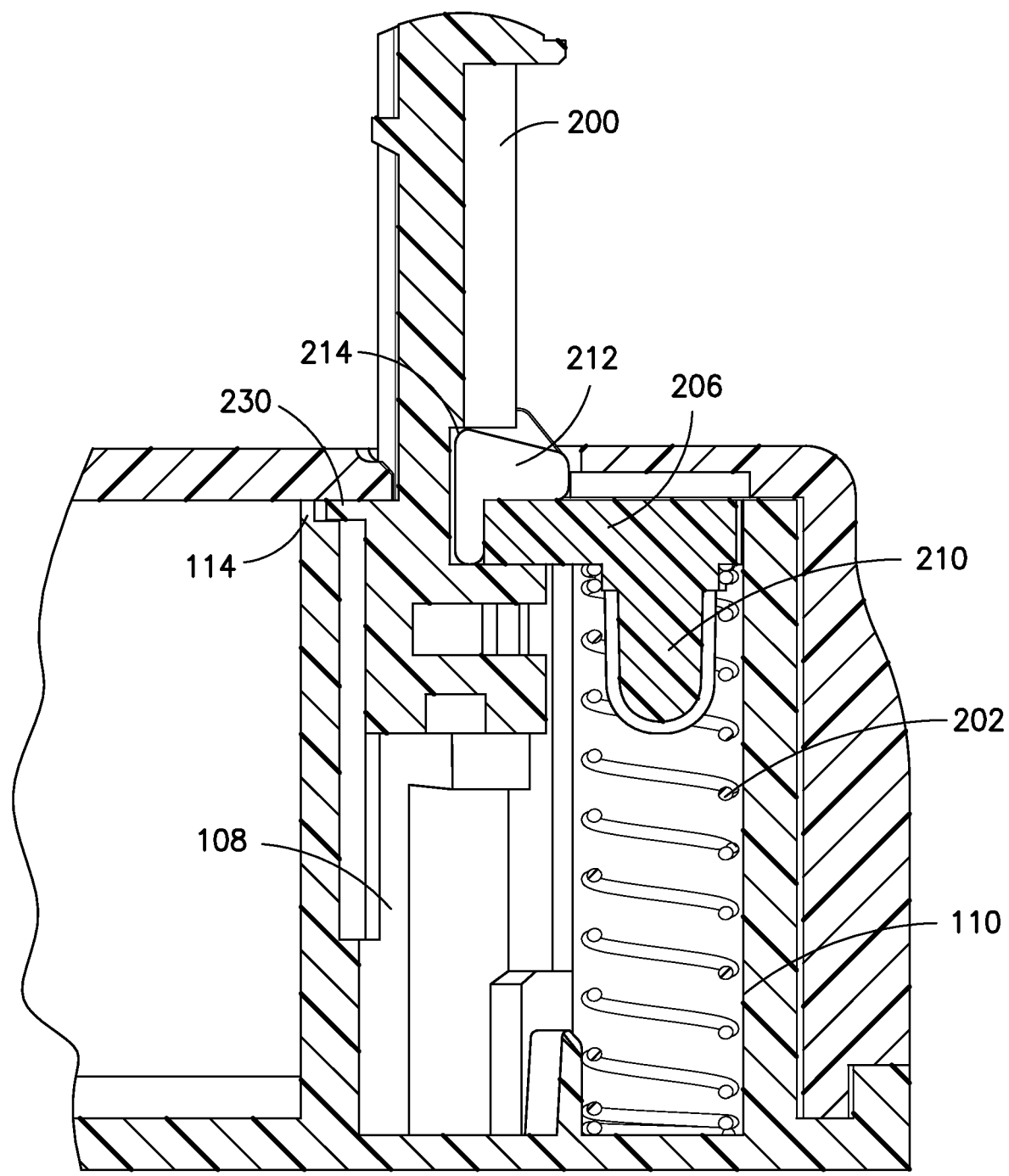
FIG. 6 is another enlarged sectional view of the insertion device of FIG. 1 illustrating an insertion button holding detent in the pre-activation state in accordance with an embodiment of the present invention.

The insertion button 200 can further comprise one or more button holding detents 230 on the insertion button 200 which hold the button in the pre-activation position as shown in FIG. 6. FIG. 6 is an enlarged sectional view of the insertion device of FIG. 1 illustrating an insertion button holding detent in the pre-activation state in accordance with an embodiment of the present invention. A safety tab (not shown) could also be positioned in the slot 208 in the insertion button 200 which would prevent accidental activation during shipping and handling of the device once it is removed from the packaging. The safety tab would be removed just prior to insertion. The detents 230 can be disposed in step detents 214 at the top of the mechanism housing 106. Further, snaps 232 (illustrated in FIG. 15) can be provided on the housing top and insertion button 200 to lock the insertion button 200 in the post activation position, which holds the catheter to a depth of about 6 mm in the skin.

During operation, the user pushes the insertion button 200 into the top housing 100. Once the detents 230 break or deformation force threshold is exceeded, the detents 230 yield and the button 200 abruptly moves downward inserting the introducer needle 204 and catheter 220, and loading the retraction spring 202. The minimum break force of the detents 230 ensures that the user pushes hard enough to fully insert the catheter. Partial activation would result in the catheter not fully inserting, the introducer needle not retracting and the catheter not locking in the post activation position.

The release of the button 200 from the detents 230 is configured to occur once a desired amount of activation force has been applied to the button 200. Since the button 200 is releasably held in the up and extended position by the engagement between the detents 230 and the step detents 114, the force applied to the button 200 by the user steadily increases for some period of time prior to release. Upon sudden release, the force upon the button 200 has reached a desired value and therefore, the button 200 is accelerated downward due to the sudden freedom to travel and the desired force applied to the button at the time of release and maintained thereafter. Such release ensures that a desired amount of downward force, speed, smoothness and angle has been applied by the user. Such activation substantially eliminates variations in the user force applied, speed, smoothness and angle thereof, and reduces insertion failure and/or discomfort to the user.

To operate the insertion device, the user applies the insertion device to a skin surface using an adhesive upon the base 102 of the device. The user then manually pushes the protruding insertion button 200 until breaking or deforming the detents 230. The insertion button 200, now suddenly free to travel, is rapidly pushed into the top housing 100 and serves to push and insert the plastic catheter 220 and introducer needle 204 into a user skin surface, and load the retraction spring 202. As the button 200 is being pushed, the introducer needle hub 206 is constrained by the interference pieces 212. However, in the post-activation state and at which time the interference pieces 212 reach the enlarged diameter 112 of the first barrel 108, the interference pieces 212 move into the enlarged diameter 112 thereby allowing the retraction spring 202 to retract the introducer needle hub 206 and introducer needle 204. In the post-activation state, the radial hole or side-port 216 of the insertion button 200 aligns with the flexible hollow septum 224 of the base 102. Within the insertion button 200, the alignment includes the aligned openings of the side-port insertion button septum 218, side-port opening 228 in the introducer needle 204, and catheter 220. The aligned openings form a sealed, uninterrupted fluid path to a pump or reservoir. The pump or reservoir then infuses medicament through the introducer needle, into the catheter and out into the patient's subcutaneous layer.

Accordingly, exemplary embodiments of the present invention use a hollow septum to connect the plastic catheter well to the fluid path which eliminates the need for a tubing connection to the well and the large space necessary in which the tubing would travel. When the catheter is moved into a completed insertion position and the introducer needle is retracted at a post-activation state, the septum well and insertion needle side port are aligned with a fluid path of a hollow septum, thereby creating an uninterrupted and sealed fluid path between an infusion pump connector or reservoir, and the catheter. Embodiments of the present invention use a hollow septum to connect the plastic catheter well to the fluid path which eliminates the need for a tubing connection to the well and the large space necessary in which the tubing would travel.

However, in yet other exemplary embodiments of the present invention, the radial hole in the insertion button and hollow septum to complete the fluid path can be omitted, and a proximal end of the introducer needle could be attached to flexible tubing which would connect to the reservoir.

The compactness of the mechanism and elimination of a catheter wedge allows for the plastic catheter to be inserted preferably perpendicular to the skin. This creates a smaller wound than an angled insertion penetrating to the same depth, such as those provide by Omnipod™ or Eros™ systems, which has the benefit of creating less scar tissue.

Additionally, it is conceivable to modify an embodiment above to include one or more additional barrels 110 to house one or more springs 202 that are actuated by a single introducer needle hub 106 having two bosses 210 (not shown). The advantage of such configuration is for the torque derived from at least two springs 202 to substantially cancel each other out to prevent potential jamming of the device.

Figure 16:
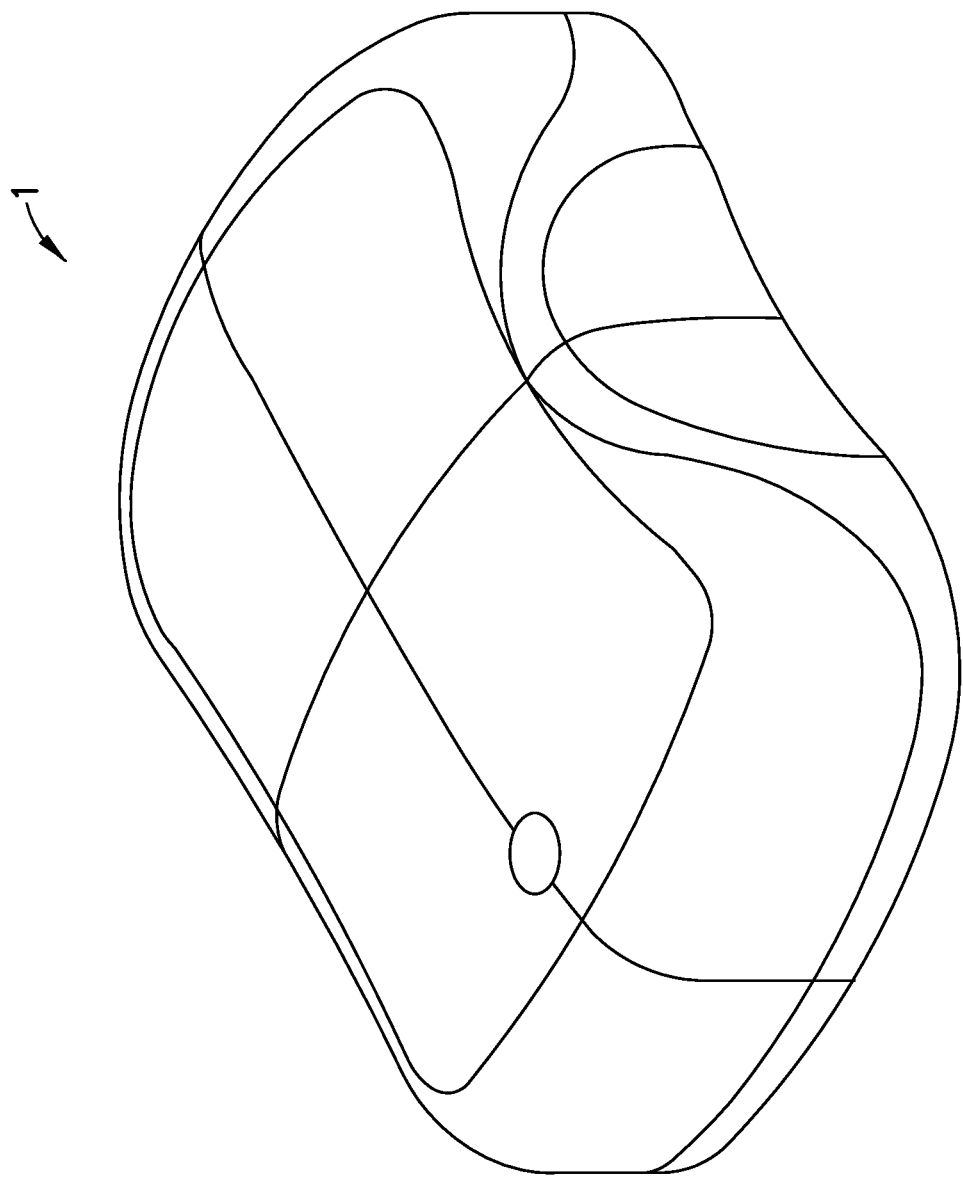
FIG. 16 is a perspective view of a patch pump incorporating a low-profile cannula insertion device.
Figure 17:
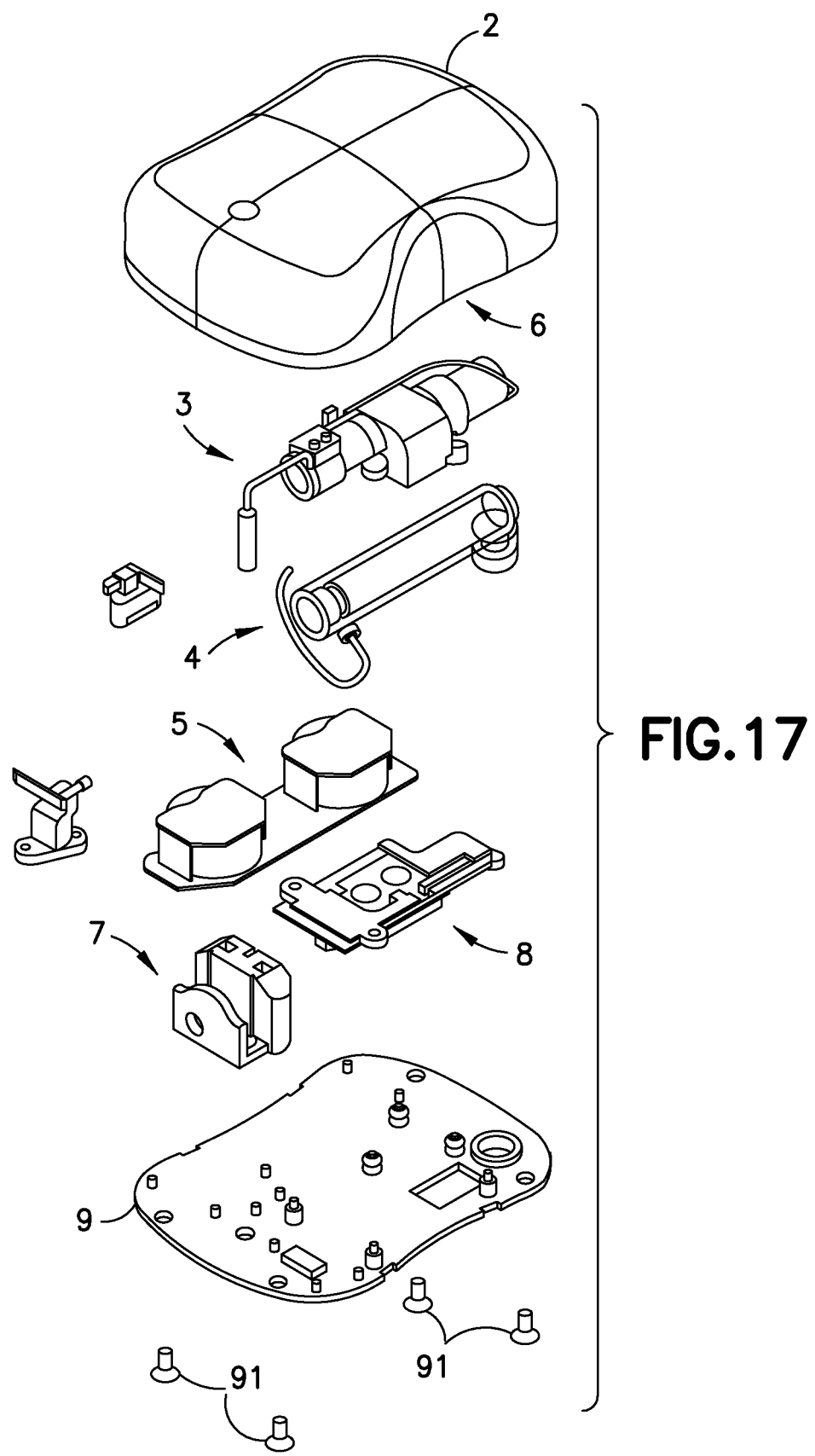
FIG. 17 is an exploded view of the various components of the patch pump of FIG. 16.

In the above embodiments, a patch pump can be provided with one or more of the described features. FIG. 16 is a perspective view of an exemplary embodiment of a patch pump 1 according to an exemplary embodiment of the invention. FIG. 17 is an exploded view of the various components of the patch pump of FIG. 16, illustrated with a solid cover 2. The various components of the patch pump 1 may include: a reservoir 4 for storing insulin; a pump 3 for pumping insulin out of the reservoir 4; a power source 5 in the form of one or more batteries; an insertion mechanism 7 for inserting an inserter needle with a catheter into a user's skin; control electronics 8 in the form of a circuit board with optional communications capabilities to outside devices such as a remote controller and computer, including a smart phone; a dose button 6 on the cover 2 for actuating an insulin dose, including a bolus dose; and a base 9 to which various components above may be attached via fasteners 91. The patch pump 1 also includes various fluid connector lines that transfer insulin pumped out of the reservoir 4 to the infusion site.

As noted above, it should be understood that inserter mechanisms come in various configurations. In some embodiments, the inserter mechanism inserts a soft catheter into the skin. In these embodiments, typically the soft catheter is supported on a rigid insertion needle. The insertion needle is inserted into the skin along with the soft catheter, and then retracted from the skin, leaving the soft catheter in the skin. In other embodiments, a soft catheter is not provided, and the insertion needle remains in the skin and forms a portion of the insulin flow path to deliver insulin until the infusion is finished. Insertion needles are typically hollow, and need to be hollow if they form part of the insulin flow path. However, insertion needles that support a soft catheter and then retract may be solid or hollow. If the insertion needle deploys a soft catheter, and retracts but remains part of the insulin flow path, then the insertion needle should be hollow. However, if the insertion needle deploys a soft catheter and then retracts but does not form part of the insulin flow path, then the insertion needle may be solid or hollow. In either case, the insertion needle is preferably rigid enough to reliably penetrate the skin, but otherwise may be made flexible enough to provide comfort to the user.

Figure 18:
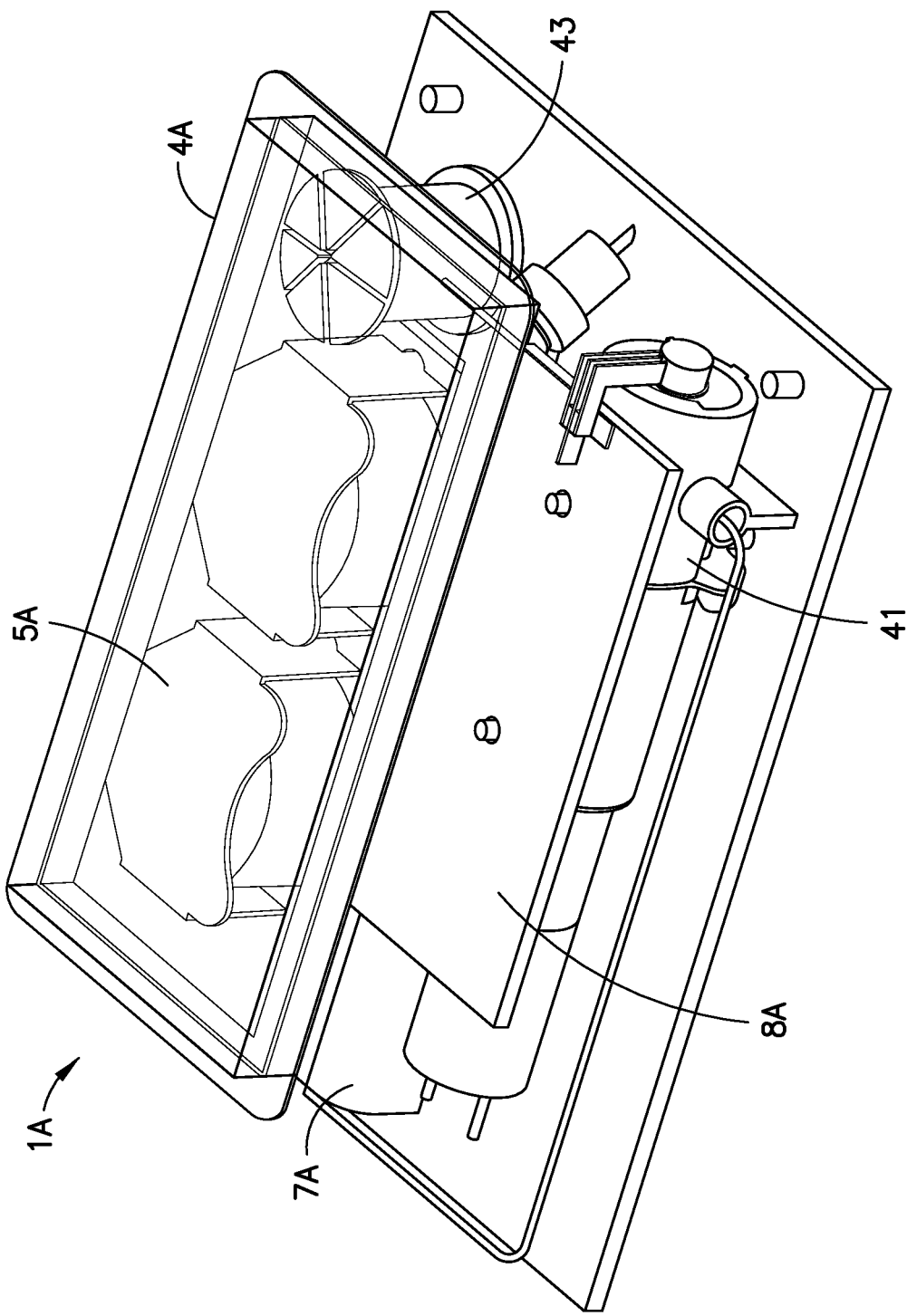
FIG. 18 is a perspective view of an alternative design for a patch pump having a flexible reservoir, illustrated without a cover.

FIG. 18 is a perspective view of an alternative design for a patch pump 1A having a flexible reservoir 4A, and illustrated without a cover. Such arrangement may further reduce the external dimensions of the patch pump 1A, with the flexible reservoir 4A filling voids within the patch pump 1A. The patch pump 1A is illustrated with a conventional cannula insertion device 7A that inserts the cannula, typically at an acute angle, less than 90 degrees, at the surface of a user's skin. The patch pump 1A further comprises: a power source 5A in the form of batteries; a metering sub-system 41 that monitors the volume of insulin and includes a low volume detecting ability; control electronics 8A for controlling the components of the device; and a reservoir fill port 43 for receiving a refill syringe 45 to fill the reservoir 4A.

Figure 19:
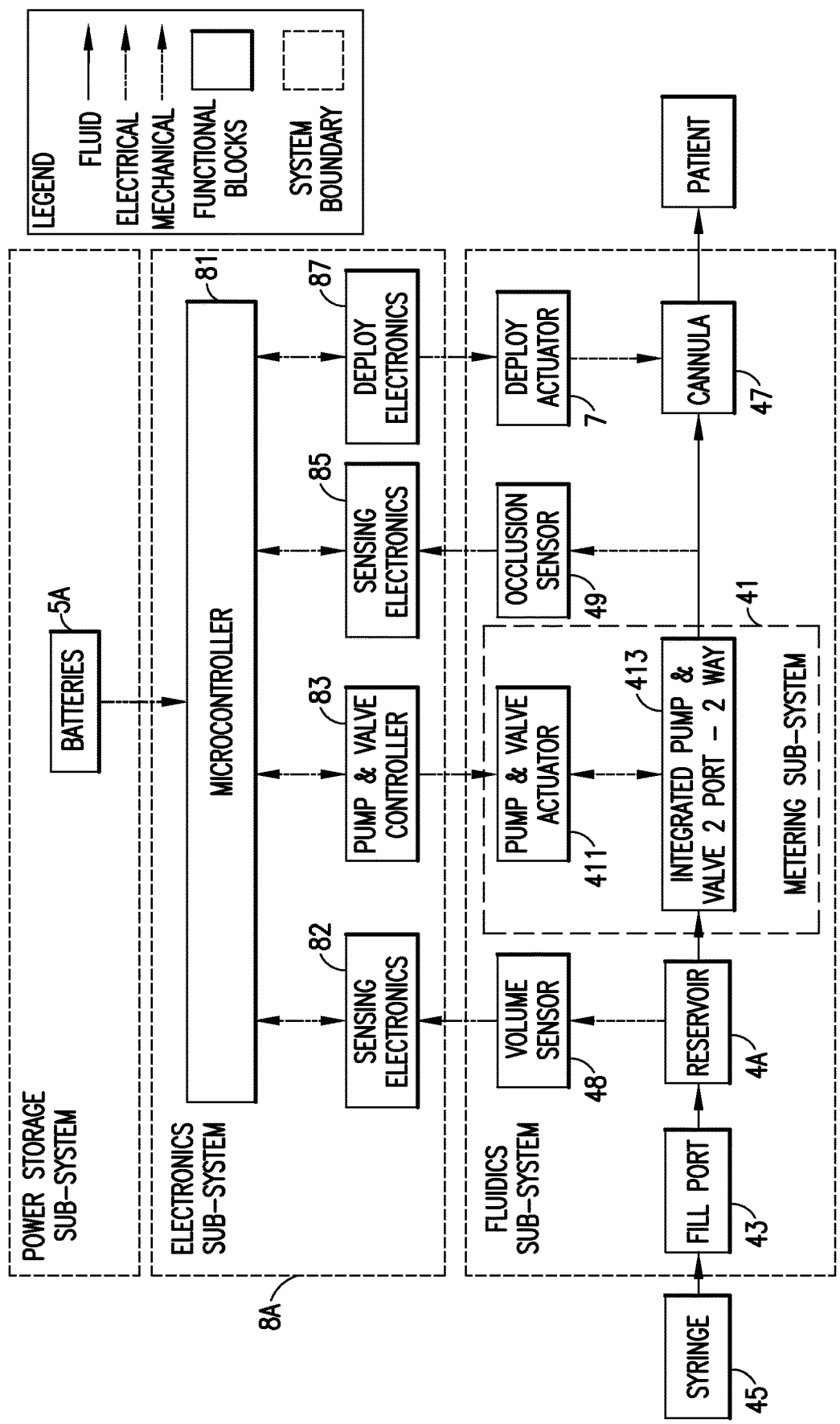
FIG. 19 is a patch-pump fluidic architecture and metering sub-system diagram of the patch pump of FIG. 18.

FIG. 19 is a patch-pump fluidic architecture and metering sub-system diagram of the patch pump 1A of FIG. 18. The power storage sub-system for the patch pump 1A includes batteries 5A. The control electronics 8A of the patch pump 1A may include a microcontroller 81, sensing electronics 82, pump and valve controller 83, sensing electronics 85, and deployment electronics 87 that control the actuation of the patch pump 1A. The patch pump 1A includes a fluidics sub-system that may include a reservoir 4A, volume sensor 48 for the reservoir 4A, a reservoir fill port 43 for receiving a refill syringe 45 to refill the reservoir 4A. The fluidics sub-system may include a metering system comprising a pump and valve actuator 411 and an integrated pump and valve mechanism 413. The fluidics sub-system may further include an occlusion sensor, a deploy actuator, as well as the cannula 47 for insertion into an infusion site on the user's skin. The architecture for the patch pumps of FIGS. 16 and 17 is the same or similar to that which is illustrated in FIG. 19.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of the appended claims and their equivalents.

The invention claimed is:

1. A catheter insertion device, comprising:
   a device housing and a button slidably captured therein;
   a catheter slidably captured by the button;
   an introducer needle subassembly comprising at least one interference piece and a needle hub, releasably secured to the button, the introducer needle subassembly originating in a first linear position; and
   a spring disposed between the device housing and the introducer needle subassembly, wherein the spring urges the introducer needle subassembly in a proximal direction from a second linear position towards a third linear position past the first linear position;
   wherein the device housing comprises a channel for slidably receiving the button, the channel having a proximal portion and a distal portion that is wider than the proximal portion; the proximal portion of the channel secures the introducer needle subassembly to the button by preventing the interference piece from moving radially;
   wherein the button comprises an inclined distal surface that contacts a proximal inclined surface of the interference piece, and urges the interference piece radially, and wherein the button moves the introducer needle subassembly and the at least one interference piece from the first linear position to the second linear position to insert the catheter and wherein the inclined distal surface of the button and the proximal inclined surface of the interference piece are both angled at an angle offset in the same relative direction from a button insertion direction; wherein the spring urges the interference piece to move radially into an expanded portion of a distal portion of the device housing corresponding to the distal portion of the channel to release the introducer needle subassembly from the button.

2. The catheter insertion device of claim 1, further comprising:
   a plurality of conjoined cylindrical openings, and wherein the button is disposed in a first cylindrical opening of the plurality of conjoined cylindrical openings, and wherein the spring is disposed in a second cylindrical opening of the plurality of conjoined cylindrical openings.

3. The catheter insertion device of claim 2, further comprising:
a boss disposed on the introducer needle subassembly, wherein the boss is disposed in the cylindrical opening concentrically with the spring.

4. The catheter insertion device of claim 1, further comprising:
a first detent disposed on the button to engage the housing, wherein the first detent is configured to secure the button in the first linear position until an activation force applied to the button exceeds a required threshold.

5. The catheter insertion device of claim 1, further comprising:
a second detent disposed on the housing to engage the button, wherein the second detent is configured to secure the button in the second linear position after an activation force has been applied to the button.

6. A catheter insertion device, comprising:
a device housing comprising a plurality of conjoined cylindrical openings;
a button slidably disposed in a first cylindrical opening of the plurality of conjoined cylindrical openings;
a retraction spring disposed in a second cylindrical opening of the plurality of conjoined cylindrical openings;
a catheter, slidably captured by the button; and
an introducer needle subassembly comprising at least one interference piece and a needle hub, releasably secured to the button,
wherein the first cylindrical opening comprises a proximal portion and a distal portion that is wider than the proximal portion;
wherein the button comprises an inclined distal surface that contacts a proximal inclined surface of the interference piece, and urges the interference piece radially, and
wherein the button moves the introducer needle subassembly and the at least one interference piece from a first linear position to a second linear position corresponding to the wider distal portion of the cylindrical opening to insert the catheter and wherein the distal inclined surface of the button and the proximal inclined surface of the interference piece are both angled at an angle offset from a button insertion direction that causes the interference piece to move radially into the wider distal portion of the cylindrical opening to release the introducer needle subassembly from the button,
wherein the retraction spring urges the introducer needle subassembly from the second linear position to a third linear position past the first linear position when the introducer needle subassembly is released from the button.

7. The catheter insertion device of claim 6, wherein when the button moves the introducer needle subassembly from the first linear position to the second linear position to insert the catheter, the introducer needle subassembly is simultaneously released from the button.

* * * * *